US011566268B2

(12) United States Patent
Clarke et al.

(10) Patent No.: US 11,566,268 B2
(45) Date of Patent: Jan. 31, 2023

(54) PROCESS FOR PRODUCING (R)-3-HYDROXYBUTYL (R)-3-HYDROXYBUTYRATE

(71) Applicants: ISIS INNOVATION LTD, Oxfordshire (GB); GOVERNMENT OF THE USA, AS REPRESENTED BY THE SECRETARY, DEPARTMENT OF HEALTH AND HUMAN SERVICES, Rockville, MD (US)

(72) Inventors: Kieran Clarke, Oxford (GB); Richard Lewis Veech, Rockville, MD (US); M. Todd King, Rockville, MD (US)

(73) Assignees: GOVERNMENT OF THE USA, AS REPRESENTED BY THE SECRETARY, DEPARTMENT OF HEALTH AND HUMAN SERVICES, Bethesda, MD (US); OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/213,713

(22) Filed: Mar. 14, 2014

(65) Prior Publication Data
US 2014/0308719 A1    Oct. 16, 2014

Related U.S. Application Data

(60) Provisional application No. 61/783,167, filed on Mar. 14, 2013.

(51) Int. Cl.
*C12P 7/62* (2022.01)
*C07C 67/03* (2006.01)
*C07C 29/147* (2006.01)

(52) U.S. Cl.
CPC .............. *C12P 7/62* (2013.01); *C07C 29/147* (2013.01); *C07C 67/03* (2013.01); *C07B 2200/07* (2013.01)

(58) Field of Classification Search
CPC ..... C07C 29/147; C07C 67/03; C07C 31/207; C07C 69/675; C07B 2200/07; C12P 7/62
See application file for complete search history.

(56) References Cited

U.S. PATENT DOCUMENTS

| | | |
|---|---|---|
| 3,984,566 A | 10/1976 | Van Scott et al. |
| 4,380,549 A | 4/1983 | Van Scott et al. |
| 5,112,865 A | 5/1992 | Nichels et al. |
| 5,281,691 A | 1/1994 | Hubbs et al. |
| 5,468,507 A | 11/1995 | Czap |
| 5,654,266 A | 8/1997 | Chen et al. |
| 5,665,831 A | 9/1997 | Neuenschwander et al. |
| 5,693,850 A | 12/1997 | Birkhahn et al. |
| 6,126,953 A | 10/2000 | Costa et al. |
| 6,136,862 A | 10/2000 | Hiraide et al. |
| 6,207,856 B1 | 3/2001 | Veech |
| 6,268,167 B1 | 7/2001 | Wild et al. |
| 6,316,038 B1 | 11/2001 | Veech |
| 6,323,237 B1 | 11/2001 | Veech |
| 6,380,244 B2 | 4/2002 | Martin et al. |
| 6,544,960 B1 | 4/2003 | Eldred et al. |
| 6,939,570 B1 | 9/2005 | Snow et al. |
| 7,351,736 B2 | 4/2008 | Veech |
| 7,947,736 B2 | 5/2011 | Gross |
| 8,101,653 B2 | 1/2012 | Veech |
| 8,642,654 B2 | 2/2014 | Clarke et al. |
| 9,034,613 B2 | 5/2015 | Robertson et al. |
| 9,211,275 B2 | 12/2015 | Clarke et al. |
| 9,579,302 B2 | 2/2017 | Veech et al. |
| 2001/0014696 A1 | 8/2001 | Veech et al. |
| 2001/0041741 A1 | 11/2001 | Sole et al. |
| 2001/0047008 A1 | 11/2001 | Baraldi |
| 2002/0006959 A1 | 1/2002 | Henderson |
| 2002/0013339 A1 | 1/2002 | Martin et al. |
| 2002/0035231 A1 | 3/2002 | Whitehouse et al. |
| 2002/0098557 A1* | 7/2002 | Muller .................. C12P 17/04 435/135 |
| 2003/0022937 A1 | 1/2003 | Veech |
| 2003/0158274 A1 | 8/2003 | Zhong et al. |
| 2004/0006263 A1 | 1/2004 | Anderson et al. |
| 2004/0063661 A1 | 4/2004 | Linnane |
| 2004/0171671 A1 | 9/2004 | Veech |
| 2004/0266872 A1 | 12/2004 | Veech |
| 2005/0129783 A1 | 6/2005 | McCleary et al. |
| 2005/0165318 A1 | 7/2005 | Brodnick et al. |

(Continued)

FOREIGN PATENT DOCUMENTS

| | | |
|---|---|---|
| CA | 1330307 C | 6/1994 |
| CA | 2173270 A1 | 10/1996 |

(Continued)

OTHER PUBLICATIONS

O'Neil et al. Tetrahedron Asymmetry (1994) 5(1): 117-118.*
Silva et al. J. Ind. Microbiol. Biotechnol. (2004) 31: 245-254.*
Seebach et al. Organic Syntheses, Coll. (1998) 9: p. 483; vol. 71 (1993): p. 39.*
Casey et al. Adv. Practical Organic Chemistry (1990) (Blackie: Glasgow and London) pp. 158-160.*
Salehizadeh et al. Biotechnol. Advances (2004) 22: 261-279.*
Kashiwaya et al. J. Biol. Chem. (2010) 285(34) 25950-29596 (Year: 2010).*
Chaikin et al. J. Am. Chem. Soc. (1949) 71(1): 122-125 (Year: 1949).*

(Continued)

*Primary Examiner* — Susan M Hanley
(74) *Attorney, Agent, or Firm* — Brian C. Trinque; Lathrop GPM LLP

(57) ABSTRACT

Embodiments of the present invention are directed to processes for the production of (R)-3-hydroxybutyl (R)-3-hydroxybyrate. Poly (R)-3-hydroxybyrate is transesterified with an alcohol, to form a first ester portion and a second ester portion. The first ester portion is reduced to the diol to form a diol portion and the diol portion is reacted with the second ester portion to produce (R)-3-hydroxybutyl (R)-3-hydroxybyrate.

13 Claims, No Drawings

(56) References Cited

U.S. PATENT DOCUMENTS

| | | |
|---|---|---|
| 2005/0181275 A1 | 8/2005 | Jang |
| 2005/0182235 A1* | 8/2005 | Zhong et al. .................. 528/361 |
| 2006/0078596 A1 | 4/2006 | Clarke et al. |
| 2006/0280721 A1 | 12/2006 | Veech et al. |
| 2007/0179197 A1 | 8/2007 | Henderson et al. |
| 2008/0287372 A1 | 11/2008 | Henderson |
| 2009/0197952 A1 | 8/2009 | Hashim et al. |
| 2009/0253781 A1 | 10/2009 | Veech |
| 2010/0298294 A1 | 11/2010 | Clarke et al. |
| 2011/0237666 A1 | 9/2011 | Clarke et al. |
| 2012/0064611 A1 | 3/2012 | Robertson et al. |
| 2012/0071548 A1 | 3/2012 | Veech |
| 2012/0213835 A1 | 8/2012 | Neas et al. |
| 2013/0102663 A1 | 4/2013 | Clarke et al. |
| 2014/0194509 A1 | 7/2014 | Clarke et al. |
| 2014/0308719 A1 | 10/2014 | Clarke et al. |
| 2015/0065571 A1 | 3/2015 | Clarke et al. |
| 2015/0164855 A1 | 6/2015 | Clarke et al. |
| 2015/0250755 A1 | 9/2015 | Veech et al. |
| 2016/0030314 A1 | 2/2016 | Clarke et al. |
| 2016/0193173 A1 | 7/2016 | Clarke et al. |

FOREIGN PATENT DOCUMENTS

| | | | |
|---|---|---|---|
| CN | 1483355 A | 9/2002 | |
| CN | 1552315 A | 12/2004 | |
| DE | 1141293 B * | 12/1962 | ............. C07C 41/26 |
| DE | 20205184 U1 | 12/2002 | |
| EP | 0 266 217 A2 | 5/1988 | |
| EP | 0 537 113 A1 | 4/1993 | |
| EP | 0552896 A1 | 7/1993 | |
| EP | 0 721 740 A1 | 7/1996 | |
| EP | 0816316 A1 * | 1/1998 | ........... C07C 29/147 |
| EP | 1568780 A1 | 8/2005 | |
| EP | 1809235 B1 | 7/2007 | |
| EP | 2 875 812 A1 | 5/2015 | |
| GB | 1524611 A | 9/1978 | |
| GB | 0312603.4 | 6/2003 | |
| GB | 0313760.1 | 6/2003 | |
| GB | 2511941 A | 9/2014 | |
| JP | S54-138126 A | 10/1979 | |
| JP | S63-112998 A | 5/1988 | |
| JP | H01-160917 A | 6/1989 | |
| JP | H03-083950 A | 4/1991 | |
| JP | 04112825 A | 4/1992 | |
| JP | H07-76513 A | 3/1995 | |
| JP | H08-191664 A | 7/1996 | |
| JP | H01-95730 A | 4/1998 | |
| JP | 10175855 A | 6/1998 | |
| JP | H10-265378 A | 10/1998 | |
| JP | H10-313819 A | 12/1998 | |
| JP | 2001-515510 A | 9/2001 | |
| JP | 2005-247821 A | 9/2005 | |
| JP | 2008-513017 A | 5/2008 | |
| JP | 2008127369 A | 6/2008 | |
| JP | 2008-263825 A | 11/2008 | |
| JP | 2009532496 A | 9/2009 | |
| JP | 2012500264 A | 1/2012 | |
| SU | 507322 A | 3/1976 | |
| WO | 198703806 A1 | 7/1987 | |
| WO | 199509144 A1 | 4/1995 | |
| WO | 1998/041201 A1 | 9/1998 | |
| WO | 1998041200 A1 | 9/1998 | |
| WO | 1999/024451 A2 | 5/1999 | |
| WO | 200004895 A2 | 2/2000 | |
| WO | 200015216 A1 | 3/2000 | |
| WO | 200113877 A | 3/2001 | |
| WO | 200151645 A | 7/2001 | |
| WO | 2002/006368 A2 | 1/2002 | |
| WO | 2003/012417 A2 | 2/2003 | |
| WO | 2003/056319 A2 | 7/2003 | |
| WO | 2003/097860 A1 | 11/2003 | |
| WO | 2004105742 A1 | 12/2004 | |
| WO | 2004108740 A2 | 12/2004 | |
| WO | 2006020137 A2 | 2/2006 | |
| WO | 2006/031941 A2 | 3/2006 | |
| WO | 2006/061624 A1 | 6/2006 | |
| WO | 2006070337 A2 | 7/2006 | |
| WO | 2007001883 A2 | 1/2007 | |
| WO | 2007063037 A2 | 6/2007 | |
| WO | 2007115282 A2 | 10/2007 | |
| WO | 2007115934 A1 | 10/2007 | |
| WO | 2008/074473 A2 | 6/2008 | |
| WO | 2008119032 A1 | 10/2008 | |
| WO | 2008140828 A1 | 11/2008 | |
| WO | 2009023357 A2 | 2/2009 | |
| WO | 2009/089144 A1 | 7/2009 | |
| WO | 2010021766 A1 | 2/2010 | |
| WO | 2010120300 A1 | 10/2010 | |
| WO | 2011101171 A1 | 8/2011 | |
| WO | 2011121540 A1 | 10/2011 | |
| WO | 2012113415 A1 | 8/2012 | |
| WO | 2013/150153 A1 | 10/2013 | |
| WO | 2014071389 A1 | 5/2014 | |
| WO | 2014/153416 A1 | 9/2014 | |

OTHER PUBLICATIONS

Kotz and P{urcell"Chemistry and Chemical Reactivity" Second edition, 1991 (Saunders College Publishing: fort Worth) pp. 113-114 (Year: 1991).*

English translation of DE 1141293B (1962) downloaded from the EPO on Jun. 3, 3021 (Year: 1962).*

Machine translation of CN 1397577 published Feb. 15, 2003 dowloaded from IP.com Dec. 22, 2021 (Year: 2003).*

Sharma et al. J. Molec. Catalysis B: Enzymatic (2000) 10: 531-534 (Year: 2000).*

Linko J. Am. Oil Chem. Soc (1995) 72(11): 1293-1299 (Year: 1995).*

Hoeng et al. Biotechnol. Bioengineer. (2000) 69(4): 379-376 (Year: 2000).*

Buteau (2009) "Obviousness of Enantiomers over Prior Art Racemates," The Journal of High Technology Law. L22. pp. 42-49.

Desrochers et al. (1992) "Metabolism of R and S-1,3-butanediol in perfused livers from meal-fed and starved rats," Biochem. J. 285:647-653.

Desrochers et al. (1995) "Metabolism of (R,S)-1,3-butanediol acetoacetate esters, potential parenteral and enteral nutrients in conscious pigs," Am. J. Physiol. 268:E660-667.

Desrochers et al. (1995) "R, S-1, 3-butanediol acetoacetate esters, potential alternates to lipid emulsions for total parenteral nutrition," Journal of Nutritional Biochemistry. 6(2):111-118.

Edegger et al. (2006) "Regio- and Stereoselective Reduction of Diketones and Oxidation of Diols by Biocatalytic Hydrogen Transfer," Eur. J. Org. Chem. 2006(8):1904-1909.

Goldbort et al. (1976) "Butanediols: Selection, open field activity, and NAD reduction by liver extracts in inbred mouse strains," Pharmacology Biochemistry and Behaviour. 5(3):263-268.

Kalaitzakis et al. (2005) "Highly Stereoselective Reductions of α-Alkyl-1,3-diketones and α-Alkyl-β-keto Esters Catalyzed by Isolated NADPH-Dependent Ketoreductases," Org. Lett. 7(22):4799-4801.

Malloy et al. (2006) "Drug Therapy of Dyslipidemia," In; Goodman & Gilman's the Pharmacological Basis of Therapeutics. 11th Ed. McGraw-Hill. New York, New York. pp. 948-953.

Puchowicz et al. (2000) "Dog model of therapeutic ketosis induced by oral administration of R,S-1,3-butanediol diacetoacetate," J. Nutr. Biochem. 11:281-287.

Shaw et al. (1984) "Influence of beta-hydroxybutyrate infusion on glucose and free fatty acid metabolism in docs," Am. J. Phys. 247:E756-764.

Tobin et al. (1972) "Effect of 1,3-Butanediol and Propionic Acid on Blood Ketones, Lipids and Metal Ions in Rats," Journal of Nutrition. 102(8):1001-1008.

Turner et al. (1999) "Glycemic control with diet, sulfonylurea, metformin, or insulin in patients with type 2 diabetes mellitus: progressive requirement for multiple therapies (UKPDS 49)," The Journal of the American Medical Association. 281(21):2005-2012.

(56) References Cited

OTHER PUBLICATIONS

Zhu et al. (2006) "A recombinant ketoreductase tool-box. Assessing the substrate selectivity and stereoselectivity toward the reduction of β-ketoesters," Tetrahedron. 62:901-905.
International Preliminary Report on Patentability corresponding to International Patent Application No. PCT/US2009/030095, dated Jul. 6, 2010.
International Preliminary Report on Patentability corresponding to International Patent Application No. PCT/US2009/040773, dated Oct. 18, 2011.
International Search Report with Written Opinion corresponding to Interntational Patent Application No. PCT/EP2011/000833, dated Jun. 22, 2011.
International Search Report with Written Opinion corresponding to Interntational Patent Application No. PCT/US2004/018016, dated Apr. 15, 2005.
International Search Report with Written Opinion corresponding to Interntational Patent Application No. PCT/US2009/030095, dated Feb. 23, 2009.
International Search Report with Written Opinion corresponding to Interntational Patent Application No. PCT/US2009/040766, dated Aug. 6, 2009.
International Search Report with Written Opinion corresponding to Interntational Patent Application No. PCT/US2009/040773, dated Feb. 22, 2010.
Supplementary European Search Report and Written Opinion corresponding to European Patent Application No. 09701051.6, dated Jan. 19, 2011.
Larios et al. (2004) "Synthesis of flavor and fragrance esters using Candida antarctica lipase," Appl. Microbiol. Biotechnol. 65:373-376.
Abdelwahab et al. (2012) "The Ketogenic Diet Is an Effective Adjuvant to Radiation Therapy for the Treatment of Malignant Glioma," PLOS ONE. 7(5):E36197. pp. 1-7.
Boyarinov et al. (1984) "Effect of Sodium hydroxybutyrate on myocardial high-energy phosphates, function, and ultrastructure after blood loss", Biulleten' eksperimental'noĭ biologii i meditsiny. 97(3):289-292.
Rossi et al. (2000) "Suppression of Feed Intake after Parenteral Administration of D—β β—Hydroxybutyrate in Pygmy Goats," J. Vet. Med. A. 47:9-16.
Clark et al. (2005) "Dilated Cardiomyopathy and Acute Liver Injury Associated with Combined Use of Ephedra, γ-Hydroxybutyrate, and Anabolic Steroids" Pharmacotherapy. 25(5):756-761.
Davey et al. (1988) "Radioprotection of rat subependymal plate with 4-OH sodium butyrate," NCI Monogr. (6):231-234.
Eagles et al. (1997) "The effects of combined treatment with β1-selective receptor antagonists and lipid-lowering drugs on fat metabolism and measures of fatigue during moderate intensity exercise: a placebo-controlled study in healthy subjects," Brit. J. Clinical Pharmacol. 43:291-300.
Felig et al. (1971) "Amino acid metabolism in exercising man," J. Clin. Invest. 50(12):2703-2714.
Kohut et al. (1995) "Effects of decreased free fatty acids on fatigue during exercise with carbohydrate feedings," Medicine and Science in Sports & Exercise. 27(5 Suppl):S102.
Kulinskii et al. (1993) "The radioprotective effect of GABA-tropic substances, gamma-hydroxybutyrate and piracetam," Radiobiologiia. 33(1):133-136.—English Abstract Only.
Kashiwaya et al. (2013) "A ketone ester diet exhibits anxiolytic and cognition-sparing properties, and lessens amyloid and tau pathologies in a mouse model of Alzheimer's disease," Neurobiology of Aging. 34(6):1530-1539.
Mori et al. (1987) "New synthesis of both enantiomers of grandisol, the boll weevil pheromon," Tetrahedron. 43(10):2229-2239.
Nair et al. (1988) "Effect of beta-hydroxybutyrate on whole-body leucine kinetics and fractional mixed skeletal muscle protein synthesis in humans," J. Clin. Invest. 82(1):198-205.

Ostrovskaya et al. (1981) "Effect of prolonged administration of sodium hydroxybutyrate on the working capacity and muscle tissue in rats," Farmakologiya I Toksikologiya. 44(5):534-539.—Only English Abstract Provided.
Sherwin et al. (1975) "Effect of ketone infusions on amino acid and nitrogen metabolism in man" J. Clin. Invest. 55(6)1382-1390.
Simons et al. (1982) "Long term treatment with Slow Release Oxprenolol Alone, or in Combination with other Drugs: Effects on Blood Pressure, Lipoproteins and Exercise Performance," Aust. N. Z. J. Med. 12:612-616.
Smith et al. (1975) "Initial effect of injury on ketone bodies and other blood metabolites," Lancet. 1(7897):1-3.
Wu et al. (1987) "Ketone bodies inhibit leucine degradationin chick skeletal muscle," International J. of Biochem. 19(10):937-943.
Neubauer et al. (1997) "Myocardial Phosphocreatine-to-ATP Ratio is a predictor of mortality in patients with dilated cardiomyopathy," Circulation. 96:2190-2196.
International Search Report with Written Opinion corresponding to International Patent Application No. PCT/EP2014/067027, dated Oct. 30, 2014.
International Search Report with Written Opinion corresponding to International Patent Application No. PCT/GB2004/002286, dated Oct. 11, 2004.
Search Report corresponding to Great Britain Patent Application No. 1002983.3, dated Jun. 10, 2010.
Search Report corresponding to Great Britain Patent Application No. 1304467.2, dated Aug. 23, 2013.
Search Report corresponding to Great Britain Patent Application No. 1314127.0, dated Jan. 31, 2014.
Search and Examination Report corresponding to Great Britain Patent Application No. 1404400.2, dated Mar. 26, 2014.
Search and Examination Report corresponding to Great Britain Patent Application No. 1414016.4, dated Aug. 29, 2014.
Search and Examination Report corresponding to Great Britain Patent Application No. 1404577.7, dated Oct. 23, 2014.
International Search Report with Written Opinion corresponding to International Patent Application No. PCT/EP2013/057250, dated Jun. 11, 2013.
International Search Report with Written Opinion corresponding to International Patent Application No. PCT/US2013/068545, dated Jan. 20, 2014.
International Search Report corresponding to International Patent Application No. PCT/EP2014/055158, dated Jun. 25, 2014.
International Search Report corresponding to International Patent Application No. PCT/EP2013/069189, dated Aug. 12, 2014.
Examination Report corresponding to Great Britain Patent Application No. 1404400.2, dated Aug. 18, 2014.
Chen et al. (Feb. 2016) "Beta-hydroxybutyrate reduces alcoholic steatohepatits (ASH) via activation of the GPR 109A Receptor," Proceedings of the American Society for Hematology, 2016. Abstract No. 26. pp. 143-144.
Farmer et al. (1973) "Radioprotective Thiazolidines from beta-keto esters," J. Med. Chem. 16(4):411-413.
Baron et al. (1991) "Mechanism of insulin resistance in insulin-dependent diabetes mellitus: a major role for reduced skeletal muscle blood flow," J. Clin. Endocrinol. Metab. 73(3):637-643.
Boehm et al. (2001) "Increased uncoupling proteins and decreased efficiency in the palmitate-perfused hyperthyroid rat heart," Am. J. Physiol. Heart Circ. Physiol. 2809(3):H977-H983.
Chatham et al. (1999) "Preferential inhibition of lactate oxidation relative to glucose oxidation in the rat heart following diabetes," Cardiovasc Res. 43(1):96-106.
Chatham et al. (2002) "Cardiac carbohydrate metabolism in Zucker diabetic fatty rats," Cardiovasc Res. 55(1):104-112.
Chen et al. (Nov. 13, 2016) "β-hydroxybutyrate protects from alcoholic hepatitis via a GPR109a-C/EBPβ dependent pathway," AASLD LiverLearning. Abstract No. 1629. Accessible on the Internet at URL: http://liverlearning.aasld.org/aasld/2016/thelivermeeting/144521/yonglin.chen.b-hydroxybutyrate.protects.from.alcoholic.hepatitis.via.a.html. [Last Accessed Apr. 5, 2017].
Cole et al. (2011) "A high fat diet increases mitochondrial fatty acid oxidation and uncoupling to decrease efficiency in rat heart," Basic Res. Cardiol. 106:447-457.

(56) References Cited

OTHER PUBLICATIONS

Cox et al. (Oct. 29, 2014) "Acute nutritional ketosis: implications for exercise performance and metabolism," Extrem. Physiol Med. 3:17. pp. 1-9.
Demir et al. (2001) "Serum HbA1c levels and exercise capacity in diabetic patients," Jpn. Heart J. 42(5):607-616.
Estacio et al. (1998) "The association between diabetic complications and exercise capacity in NIDDM patients," Diabetes Care. 21(2):291-295.
Frayn (2003) In; Metabolic Regulation: A Human Perspective. 2nd Ed. Blackwell Science, pp. 94-96.
Gangemi "Enhancing Athletic Performance by Predicting Fatigue and Preventing Muscle Failure," Accessible on the Internet at URL: http://www.drgangemi.com/wp-content/uploads/2011/01/GANGEMI-PREDICTING-FATIGUE-AND-MUSCLE-FAILURE.pdf. [Last Accessed Sep. 20, 2011].
Iozzo et al. (2002) "Mismatch between insulin-mediated glucose uptake and blood flow in the heart of patients with Type II diabetes," Diabetologia. 45(10):1404-1409.
Kemper et al. (Oct. 26, 2015) "An Ester of β-Hydroxybutyrate Regulates Cholesterol Biosynthesis in Rats and a Cholesterol Biomarker in Human," Lipids. 50(12):1185-1193.
Knowler et al. (2002) "Reduction in the incidence of type 2 diabetes with lifestyle intervention or metformin," New Engl. J. Med. 346:393-403.
Komiyama et al. (2000) "Near-infrared spectroscopy grades the severity of intermittent claudication in diabetes more accurately than ankle pressure measurement," British Journal of Surgery. 87(4):459-466.
Komiyama et al. (2004) "Effects of a 4-week 70% high carbohydrate / 15% low fat diet on glucose tolerance and on lipid profiles," Diabetes Res. Clin. Pract. 64(1):11-18.
Kwiterovich et al. (2003) "Effect of a high-fat ketogenic diet on plasma levels of lipids, lipoproteins, and apolipoproteins in children," JAMA. 290(7):912-920.
Lanni et al. (2002) "De Novo Expression of Uncoupling Protein 3 is Associated with Enhanced Mitochondrial Thioesterase-1 Expression and Fatty Acid Metabolism in Liver of Fenofibrate-treated Rats," FEBS Letters. 525:7-12.
Libby et al. (2002) "Diabetic macrovascular disease. The glucose paradox?" Circulation. 106(22):2760-2763.
Lodi et al. (1999) "Reduced cytosolic acidification during exercise suggests defective glycolytic activity in skeletal muscle of patients with Becker muscular dystrophy. An in vivo 31P magnetic resonance spectroscopy study," Brain. 121(1):121-130.
Madsen et al. (1999) "Near-infrared oximetry of the brain," Prog. Neurobiol. 58(6):541-560.
Mahler et al. (1999) "Type 2 diabetes mellitus: update on diagnosis, pathophysiology, and treatment," J. Clin. Endocrinol. Metab. 84(4):1165-1171.
Meyer et al. (1997) "Myocardial blood flow and glucose metabolism in diabetes mellitus," Am. J. Cardiol. 80(3,Suppl 1):94A-101A.
Mori et al. (1984) "Synthesis of the Propionates of (2R, 8R)- and (2S, 8R)-8-methyl-2-decanol, the pheromone of the Western corn rootworm, employing chiral compounds of microbial origin as starting material," Tetrahedron. 40(2):299-303.
Murray et al. (2004) "Uncoupling Proteins in Human Heart," Lancet. 364:1786-1788.
Murray et al. (2005) "Plasma Free Fatty Acids and Peroxisome Proliferator-Activated Receptor a in the Control of Myocardial Uncoupling Protein Levels," Diabetes. 54(12):3496-3502.
Newsholme et al. (1986) In; Biochemistry for the Medical Sciences. John Wiley & Sons. Chichester, U.K. pp. 324-331.
Paolisso et al. (1999) "Prognostic importance of insulin-mediated glucose uptake in aged patients with congestive heart failure secondary to mitral and/or aortic valve disease," Am. J. Cardiol. 83(9):1338-1344.
Perez-Jimenez et al. (2001) "A Mediterranean and a high-carbohydrate diet improve glucose metabolism in healthy young persons," Diabetologia. 44(11):2038-2043.
Richieri et al. (1995) "Unbound free fatty acid levels in human serum," Journal of Lipid Research. 36(2):229-240.
Rodrigues et al. (1998) "Metabolic disturbances in diabetic cardiomyopathy," Molecular and Cellular Biochemistry. 180(1-2):53-57.
Sato et al. (1995) "Insulin, ketone bodies, and mitochondrial energy transduction," Faseb J. 9(8):651-658.
Scheuermann-Freestone et al. (2003) "Abnormal cardiac and skeletal muscle energy metabolism in patients with type 2 diabetes," Circulation. 107(24):3040-3046.
Sidell et al. (2002) "Thiazolidinedione treatment normalizes insulin resistance and ischemic injury in the Zucker fatty rat heart," Diabetes. 51(4):1110-1117.
Smith et al. (2002) "Magnetic Resonance Spectroscopy in Medicine: Clinical Impact," Progress in Nuclear Magnetic Resonance Spectroscopy. 40:1-34.
Stanley et al. (1997) "Regulation of energy substrate metabolism in the diabetic heart," Cardiovasc. Res. 34(1):25-33.
Taegtmeyer et al. (2002) "Adaptation and maladaptation of the heart in diabetes: Part I. General concepts," Circulation. 105(14):1727-1733.
Tinnikov et al. (1999) "Colorimetric micro-determination of free fatty acids in plasma using microplate readers," Clinica Chemica Acta. 281(1-2):159-162.
Toubro et al. (1998) "Twenty-four-hour respiratory quotient: the role of diet and familial resemblance," J. Clin. Endocrinol. Metabol. 83(8):2758-2764.
Tunaru et al. (2003) "PUMA-G and HM74 are receptors for nicotinic acid and mediate its anti-lipolytic effect," Nat. Med. 9(3):352-355.
Zange et al. (2002) "Creatine Supplementation Results in Elevated Phosphocreatine/Adenosine Triphosphate (ATP) Ratios in the Calf Muscle of Athletes but Not in Patients with Myopathies," Annals of Neurology. 53(1):126-127.
International Search Report with Written Opinion corresponding to International Patent Application No. PCT/EP2013/069189, dated Aug. 12, 2014.
International Search Report with Written Opinion corresponding to International Patent Application No. PCT/EP2014/055158, dated Jun. 25, 2014.

* cited by examiner

PROCESS FOR PRODUCING (R)-3-HYDROXYBUTYL (R)-3-HYDROXYBUTYRATE

GOVERNMENT LICENSE RIGHTS

The present application was made with government support under Grant No. W911NF-05-1-0479 awarded by ARMY/ARO. The government has certain rights in this invention.

The invention relates to a process for producing (R)-3-hydroxybutyl (R)-3-hydroxybutyrate. In particular, the invention relates to a process for producing (R)-3-hydroxybutyl (R)-3-hydroxybutyrate from a single starting material feedstock of poly-(R)-3-hydroxybutyrate.

Ketone bodies are chemical compounds which are produced by the liver from fatty acids released from adipose tissue. Ketone bodies themselves can be used as a source of energy in most tissues of the body. The intake of compounds that boost the levels of ketone bodies in the blood can lead to various clinical benefits, including an enhancement of physical and cognitive performance and the treatment of cardiovascular conditions, diabetes, neurodegenerative diseases and epilepsy. Ketone bodies include (R)-3-hydroxybutyrate and acetoacetate.

WO2004/108740 discloses that ketone bodies may be administered directly to achieve elevated levels of ketone bodies in a subject. However, direct administration of the compounds is unpractical and potentially dangerous. For example, direct administration of either (R)-3-hydroxybutyrate or acetoacetate in its free acid form can result in significant acidosis following rapid absorption from the gastrointestinal tract. Administration of the sodium salt of these compounds in unregulated amounts is also unsuitable due to a potentially dangerous sodium overload that could accompany administration of therapeutically relevant amounts of the compounds. Examples of the derivatives include esters, for instance esters derived from a variety of alcohols and oligomers of (R)-3-hydroxybutyrate.

WO2010021766 discloses that one particular enantiomer of one particular ester of 3-hydroxybutyrate is an effective and palatable precursor to the ketone body (R)-3-hydroxybutyrate. Thus WO2010021766 discloses 3-hydroxybutyl 3-hydroxybutyrate enantiomerically enriched with respect to (R)-3-hydroxybutyl (R)-3-hydroxybutyrate.

Various synthetic approaches have been developed for the production of this stereoisomer. Methods are known for producing hydroxybutyrate from poly-(R)-3-hydroxybutyrate but involve a large number of steps and are complex. Other synthetic approaches have been attempted but have various technical and commercial drawbacks including low yields, the production of impure product, impracticability on a large scale and cost.

WO2010/120300 discloses various methods of a producing (R)-3-hydroxybutyl (R)-3-hydroxybutyrate involving enantioselective reduction of a compound of formula I, II or III.

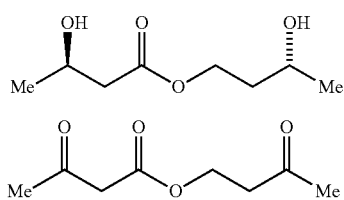

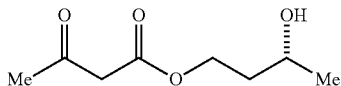

WO2010/120300 also discloses a process involving treating HOCH$_2$CH$_2$COCH$_3$ with a diketene of formula VI in WO2010120300, CH2=C(CH2)—O—C=O and subjecting the reaction to enantioselective reduction. Further processes involving treating butane-1,3-diol with the ketene VI with enantioselective reduction and a process starting from 4-hydroxybutanone are also disclosed. The enantioselective reduction is carried out using a ketoreductase or alcohol dehydrogenase.

Whilst effective at producing (R)-3-hydroxybutyl (R)-3-hydroxybutyrate these starting materials may be costly and higher rates of reaction may be desirable. There remains a need to be able to produce (R)-3-hydroxybutyl (R)-3-hydroxybutyrate at higher volumes and to improve the economics of production.

We have now found that these problems may be addressed by subjecting poly-(R)-3-hydroxybutyrate, a relatively low cost starting material, to a process that involves transesterification divides the starting material or feedstock into two portions or streams, producing a reduced intermediate from a first portion or stream, which is then reacted with a second portion or stream to provide (R)-3-hydroxybutyl (R)-3-hydroxybutyrate. In a first aspect the invention provides a process for the production of (R)-3-hydroxybutyl (R)-3-hydroxybutyrate comprising:

(i) contacting poly-(R)-3-hydroxybutyrate with an alcohol to transesterify the poly-(R)-3-hydroxybutyrate under transesterification conditions to produce an ester of (R)-3-hydroxybutyrate and the alcohol;

(ii) separating the product of step i) into a first and second portion and reducing the first portion of the (R)-3-hydroxybutyrate ester to form (R)-1,3-butanediol;

(iii) contacting under transesterification conditions the (R)-1,3-butanediol from step ii) with the second portion of the transesterified ester to produce (R)-3-hydroxybutyl (R)-3-hydroxybutyrate.

The process allows industrial scale production of enantiomerically enriched monoester of (R)-3-hydroxybutyric acid and (R)-1,3-butanediol from bulk poly-(R)-3-hydroxybutyrate which is commercially available in large scale and acceptable cost, for example by fermentation of corn starch or sugar cane.

The term "enriched", as employed herein, means that the level of the enriching isomer is higher than the level at which that isomer would be present in a racemic mixture. Where a percentage enrichment is referred to, the enriching isomer constitutes that molar percentage of the total 3-hydroxybutyl 3-hydroxybutyrate product present.

Preferably enantiomeric purity is measured using chiral high performance liquid chomatography (chiral HPLC). Measurements are typically made against the corresponding racemic mixture. Alternatively, chiral gas chomatography (chiral GC) may be used reliably. Accordingly, where a percentage enrichment is referred to herein, the percentage enrichment is typically that measured by chiral HPLC or by chiral GC. Preferably, the percentage enrichment is that measured by chiral HPLC. Usually, the enzyme employed is one which is capable of reducing said compound of formula (II), (III) or (IV) to produce 3-hydroxybutyl 3-hydroxybutyrate which is enantiomerically enriched to at least 95%, for instance to at least 97%, to at least 98%, or to at least 99%, with respect to (R)-3-hydroxybutyl(R)-3hydroxybutyrate.

The process may be continuous or batch. Advantageously, the invention enables a high throughput industrial production of (R)-3-hydroxybutyl (R)-3-hydroxybutyrate from poly-(R)-3-hydroxybutyrate which may be obtained from corn starch.

Preferably, the poly-(R)-3-hydroxybutyrate feedstock is provided from a single feedstock by fermentation of corn starch with microorganisms.

The poly-(R)-3-hydroxybutyrate feedstock may be transesterified in step i) using any suitable alcohol which allows the formed ester to be reduced to (R)-1,3-butanediol. Suitably a dihydric or trihydric alcohol is employed but preferably the alcohol is monohydric, for example a C1-6 alcohol. Where (R)-3-hydroxybutyl (R)-3-hydroxybutyrate is for consumption for example as a food or nutritional supplement, the alcohol is suitably ethanol as this is more acceptable for consumption than other alcohols.

Suitably, the alcohol is present in sufficient quantity that poly-(R)-3-hydroxybutyrate moieties may be esterified. Preferably the weight ratio of alcohol to poly-(R)-3-hydroxybutyrate is from 1:1 to 10:1, more preferably from 2:1 to 6:1.

The transesterification in step i) is suitably carried out in acidic conditions. Preferably, the reaction mixture comprises an acid catalyst. The acid may be organic or inorganic and is preferably a mineral acid, for example sulphuric acid. The catalyst may be solid as desired.

Suitably the transesterification is carried out at elevated temperature, preferably greater than 50° C., greater than 90° C. and desirably not more than 150° C. Elevated pressure may be employed. Suitably, the transesterification is carried out for sufficient time to affect transesterification to an economically acceptable degree having regard to the temperature, catalyst and alcohol employed. Preferably, the transesterification step is carried out for at least 1 hour, more preferably at least 10 hours, and especially 15 to 30 hours, for example 20 hours, 22 hours and 24 hours.

The product of the transesterification reaction may then be treated by one or more optional steps including filtering, purification, for example by distillation and neutralisation for example by the addition of base for example hydroxide, bicarbonate and acetate, particularly calcium hydroxide or sodium bicarbonate to neutralise the acid present.

Suitably, the ester of (R)-3-hydroxybutyrate is separated from the reaction mixture by removal of alcohol and optionally by-products of the reaction. The separation may be carried out in multiple stages as desired. In a preferred embodiment, the ester is separated and purified from the alcohol and reaction by-products. The ester may be separated from unreacted alcohol and other undesired materials, for example alkyl crotonate by separation of the liquid phase, for example by distillation of the alcohol and alkyl crotonate. The alcohol and by-products may be removed by multiple distillations, suitably at atmospheric pressure and at a temperature above the boiling point of the alcohol, for example greater than 80° C., greater than 110° C. for example at a temperature of 110 to 150° C. The ester of (R)-3-hydroxybutyrate is then suitably separated to provide a first portion which is subjected to a reduction reaction. The reduction in step ii) may be a hydride transfer reduction, hydrogenation, hydrosilylation followed by silyl ether hydrolysis. Preferably the reduction is carried out with any suitable reducing agent for reducing an ketoester. The reducing agent may be organic or inorganic. The reduction step may be mediated by an enzyme, for example a ketoreductase (KRED) or an alcohol dehydrogenase (ADH), and may be naturally occurring or commercially available, for example as described in WO2010/120300.

The reducing agent may comprise hydrogen and a hydrogenation catalyst may be employed, for example Raney nickel, desirably employed at elevated pressure and temperature and catalysts comprising platinum, palladium, rhodium, iridium or ruthenium. Preferably the reducing agent employs a hydride transfer reagent. Examples of suitable reducing agents include complex metal hydrides for example, lithium aluminium hydride, lithium tetrahydridoaluminate, sodium bis (2-methoxyethoxy) aluminium hydride, sodium borohydride, nickel borohydride, other inorganic reducing agents, for example, sodium hydrosulphite, sodium tetrahydroborate and ruthenium hydrogenation catalysts known in the art, for example ruthenium hydride and rhodium hydrogenation catalysts known in the art, aluminium triisopropoxide, and organic reducing agents including a chiral borane, for example 2,5-dimethylborolane, borontrihydride:tetrahydrofuran caticholborane, and enzymes and cofactors, for example nicotinamide adenine dinucleotide (NADH) and nicotinamide adenine dinucleotide phosphate (NADPH). As desired a cofactor recycling system is suitably employed.

The reducing step is suitably carried out under reducing conditions. A solvent may be employed. The solvent may be anhydrous, for example diethyl ether or tetrahydrofuran, or may be carried out in polar protic solvent, for example water, alcohol and basic aqueous media, depending upon the reducing agent.

Preferably, the reducing step is carried out in aqueous solution and a moderately strong reducing agent is employed so as to ensure retention of the desired stereochemistry. Desirably, the temperature of the reducing step is controlled to avoid significant temperature rise, and is desirably carried out at a temperature below standard temperature, desirably under 10° C., for example −5 to 3 C.

Suitably, the reducing agent is contacted with the first portion slowly to avoid undue temperature rise. The reducing agent and first portion are suitably allowed to react over an extended period of time, for example at least 30 minute, preferably at least 1 hour, more preferably 1 to 20 hours, especially 4 to 10 hours. Upon completion of the reduction reaction to the desired degree, the reaction may be quenched by addition of a quenching agent, for example by addition of acid, for example sulphuric acid and allowed to stand for a period of time, for example at least 1 hour, preferably 1 to 20 hours, for example overnight. Thereafter, the reaction mixture may be contacted with a removal agent, for example hydroxide and especially calcium hydroxide to remove salts of the reducing agent and quenching agent.

The butanediol produced from the first portion is then contacted with the second portion of the ester of (R)3-hydroxybutanoate.

The transesterification is suitably carried out in the presence of a transesterification catalyst, for example an enzyme, acid or base. Suitable examples of enzymes include lipase, examples of suitable acids include mineral acids for example sulphuric acid and hydrochloric acid, examples of suitable bases include alkali metal hydroxides and alkali metal alkoxides.

Preferably, the transesterification reaction between the second portion and (R)-1,3-butanediol is carried out at elevated temperature, for example from 30 to 150° C., particularly 40 to 100° C.

This transesterification process may be carried out in a batch or continuous process.

Suitably the transesterification process is carried out for at least 1 hour, preferably 1 to 20 hours, for example 5 to 10 hours. Upon completion of the reaction to the desired degree, the product of the reaction may then be subjected to further treatment to remove catalyst, unreacted starting materials and by-products, for example by filtering, distillation or the like.

The invention will be illustrated by the following non-limiting examples.

EXAMPLE 1

Transesterification Step i)

A 5 gallon Parr reactor is charged with 12.5 L (10 kg) absolute ethanol and 2.5 kg poly (R)-3-hydroxybutanoate (Biocycle, Fazenda de Pedra, c Postal 02 CEP 14158-00, Serenaa, S.P. Brazil) and stirred for 2-5 min to complete mixing after which 0.1 L concentrated sulfuric acid is added slowly to the mixture. The mixture is heated with a 300° C./h ramp to 110° C. and the reactor held in soak mode for a total run time is 22 h. The unit is cooled to about 30° C. using chilled water. After the temperature has fallen below 60° C., the digester is vented and purged with nitrogen to remove formed ether. An amount of base, equal to the equivalents of acid is added to the crude digest with stirring to neutralize the acid. Stirring is continued about 16 h after which the stirring is stopped and the solids left to settle. The liquid phase is siphoned off into a wiped film distillation apparatus and distilled in phases to remove first the ethanol and ethyl crotonate (a side product), and then the ethyl (R)-3-hydroxybutyrate. Ethanol/ethyl crotonate is distilled off over 3 passes generally at atmospheric pressure and band heater and pump flow rates of 120 & 5 L/h, 120 & 3 L/h and 140 & 3 L/h respectively. The ethyl (R) 3-hydroxybutyrate is distilled at 10 mmHg, band heater=88 and feed rate 4 L/h. The primary chiller is set to 5° C. and the secondary chiller at −1° C. for all distillations. The trap is charged with dry ice and either acetone or IPA. When collecting the ethyl (R) 3-hydroxybutyrate, the residue from the first pass is recycled through the still to recover more product. The ethyl-(R)-3-hydroxybutyrate is assayed by GC-MS and NMR for purity.

Reduction Step ii)

A heavy duty stainless steel stock pot is charged with 12 L water and a portion of (3.49 L) ethyl (R) 3-hydroxybutyrate. Both water and ester were previously chilled to 4° C. for at least 24 h. The stock pot is surrounded by ice, gassed with nitrogen and stirred. After about 1 h, 1 Kg sodium borohydride is added in small aliquots to order to minimize temperature gain. Borohydride addition takes about 1 h and the temperature should be kept below 20° C. during the NaBH$_4$ addition. About 5 h after borohydride addition the reaction is quenched by slowly adding 745 ml concentrated sulfuric acid. The mixture is allowed to stand, with stirring overnight and the temperature rise to room temperature. The mixture is filtered, the filtrate heated to 90° C. and neutralized* by adding calcium hydroxide with stirring. After 2 hours mixture is cooled and filtered and the filtrate ionic strength reduced using ion exchange resins after which the solution is placed on a Buchi Rotovap and the bulk of the water removed. This leaves a viscous liquid assaying to >10 M (R) 1,3-butanediol and containing 5-10% water. Remaining water is removed by nitrogen purge or distillation. The purity is checked by enzymatic assay, GC-MS and NMR.

Transesterification Using R-1,3-Butanediol

A solution is prepared by combining and mixing 600 ml of (R) 1,3-butanediol and 1200 ml of ethyl (R)-3-hydroxybutanoate in a stainless steel pan. A nylon mesh "tea bag" containing lipase is laid in the solution and the pan is placed on a heating pad set to 40° C. The "tea bag" is sewn with lanes to keep the enzyme dispersed. The reaction is carried out under nitrogen with agitation. After 6 h the reaction is stopped by removing the "tea bag" and collecting the solution. The solution is passed through a filter to remove any enzyme resin "fines" and collected. Once enough crude solution has been collected the solution is distilled sequentially to first degas and remove any remaining ethanol, then to remove ethyl (R)-3-hydroxybutanoate, (R) 1,3-butanediol and finally to collect the desired pure ketone ester, (R)-3-hydroxybutyl (R)-3-hydroxybutyrate. Recovered ethyl (R)-3-hydroxybutanoate and (I) 1,3-butanediol are recycled in subsequent transesterification experiments. Crude solutions and still fractions are analyzed by GC-MS.

The invention claimed is:

1. A process for the production of (R)-3-hydroxybutyl-(R)-3-hydroxybutyrate from a single starting material feedstock of poly-(R)-3-hydroxybutyrate, comprising:
   (i) contacting the poly-(R)-3-hydroxybutyrate with an alcohol to transesterify the poly-(R)-3-hydroxybutyrate under transesterification conditions to produce an ester of (R)-3-hydroxybutyrate and the alcohol, wherein the transesterification is carried out between 1 hour and 30 hours;
   (ii) separating the product of step i) into a first and second portion and reducing the first portion in a solvent using a ketoreductase or an alcohol dehydrogenase to form (R)-1,3-butanediol; and
   (iii) contacting under enzyme-catalyzed transesterification conditions the (R)-1,3-butanediol from step ii) with the second portion of the transesterified ester to produce (R)-3-hydroxybutyl-(R)-hydroxybutanoate, wherein the enzyme-catalyzed transesterification is carried out between 1 hour and 20 hours.

2. The process according to claim 1, wherein the poly-(R)-3-hydroxybutyrate is obtained from corn starch or sugar cane.

3. The process according to claim 1, wherein the poly-(R)-3-hydroxybutyrate is transesterified in step (i) using ethanol.

4. The process according to claim 1, wherein the weight ratio of alcohol to poly-(R)-3-hydroxybutyrate is from 1:1 to 10:1.

5. The process according to claim 1, wherein the step (i) is carried out in acidic conditions.

6. The process according to claim 1 wherein the product of step (i) is treated to neutralize the acid and remove the alcohol by distillation.

7. The process according to claim 6 wherein the distillation is carried out at a temperature of 110° C. to 150° C.

8. The process of claim 1, wherein prior to contacting in step (i), the process comprises fermenting a single starting material feedstock to produce the poly-(R)-3-hydroxybutyrate, wherein the feedstock is corn starch or sugar cane.

9. The process of claim 8, wherein the feedstock is corn starch.

10. The process of claim 8, wherein the feedstock is sugar cane.

11. The process of claim 8, wherein the fermenting comprises using at least one microorganism.

12. The process of claim 1, wherein the reaction mixture of step (i) comprises an acid catalyst.

13. The process of claim 1, wherein the enzyme-catalyzed transesterification in step (iii) is carried out in the presence of lipase.

* * * * *